(12) United States Patent
Brinton

(10) Patent No.: US 6,780,646 B1
(45) Date of Patent: Aug. 24, 2004

(54) METHOD FOR DETERMINING THE STORABILITY OF A GRAIN OR OILSEED SAMPLE

(76) Inventor: William F. Brinton, 20 Old Rome Rd., Mt. Vernon, ME (US) 04352

( * ) Notice: Subject to any disclaimer, the term of this patent is extended or adjusted under 35 U.S.C. 154(b) by 0 days.

(21) Appl. No.: 10/403,212

(22) Filed: Apr. 1, 2003

(51) Int. Cl.[7] .......................... G01N 33/02; G01N 31/22
(52) U.S. Cl. .......................... 436/20; 436/133; 436/163; 436/164; 436/169; 436/181; 422/55; 422/56; 422/75; 422/83; 422/86
(58) Field of Search .......................... 436/20, 127, 133, 436/163, 164, 169, 181; 422/56, 75, 82.05, 83, 86, 87, 61, 55

(56) References Cited

U.S. PATENT DOCUMENTS

| | | | |
|---|---|---|---|
| 3,899,295 A | * | 8/1975 | Halpern ...................... 422/56 |
| 4,025,309 A | * | 5/1977 | Hach .......................... 436/115 |
| 4,945,060 A | * | 7/1990 | Turner et al. ............. 435/288.7 |
| 5,124,129 A | * | 6/1992 | Riccitelli et al. ............. 422/56 |
| 5,320,807 A | * | 6/1994 | Brinton et al. ................ 422/61 |
| 5,439,648 A | * | 8/1995 | Balderson et al. ............ 422/86 |
| 5,547,987 A | * | 8/1996 | Bland et al. ................ 514/557 |
| 5,648,231 A | * | 7/1997 | King ........................... 435/34 |

OTHER PUBLICATIONS

Lupano et al. "A Simple and Rapid Test for Drying Damage in Wheat", Cereal Chemistry, vol. 65(1), 1988, pp. 49–51.*

* cited by examiner

Primary Examiner—Maureen M. Wallenhorst

(57) ABSTRACT

The rate of carbon dioxide release from a grain sample can be measured by placing the grain sample in a sealed container, and positioning a pH responsive color-change material in the container so that carbon dioxide released from the grain sample chemically reacts with a buffer incorporated into the color-change material. Carbon dioxide measurements can be used to measure actual and potential spoilage of the grain associated with fungal attack.

4 Claims, 1 Drawing Sheet

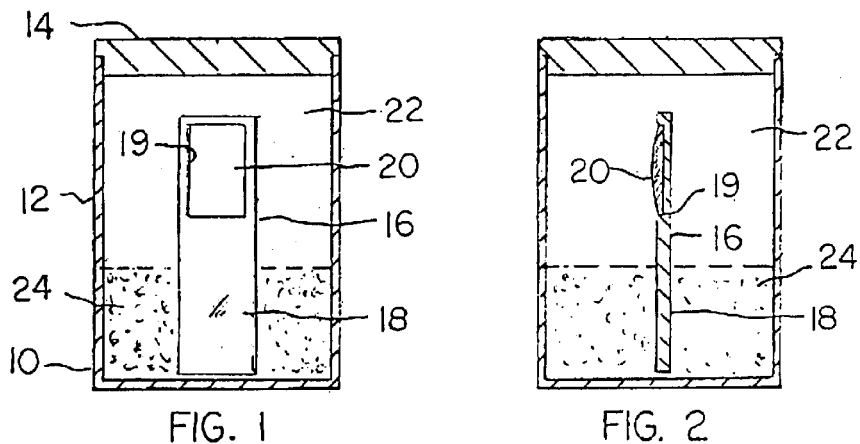
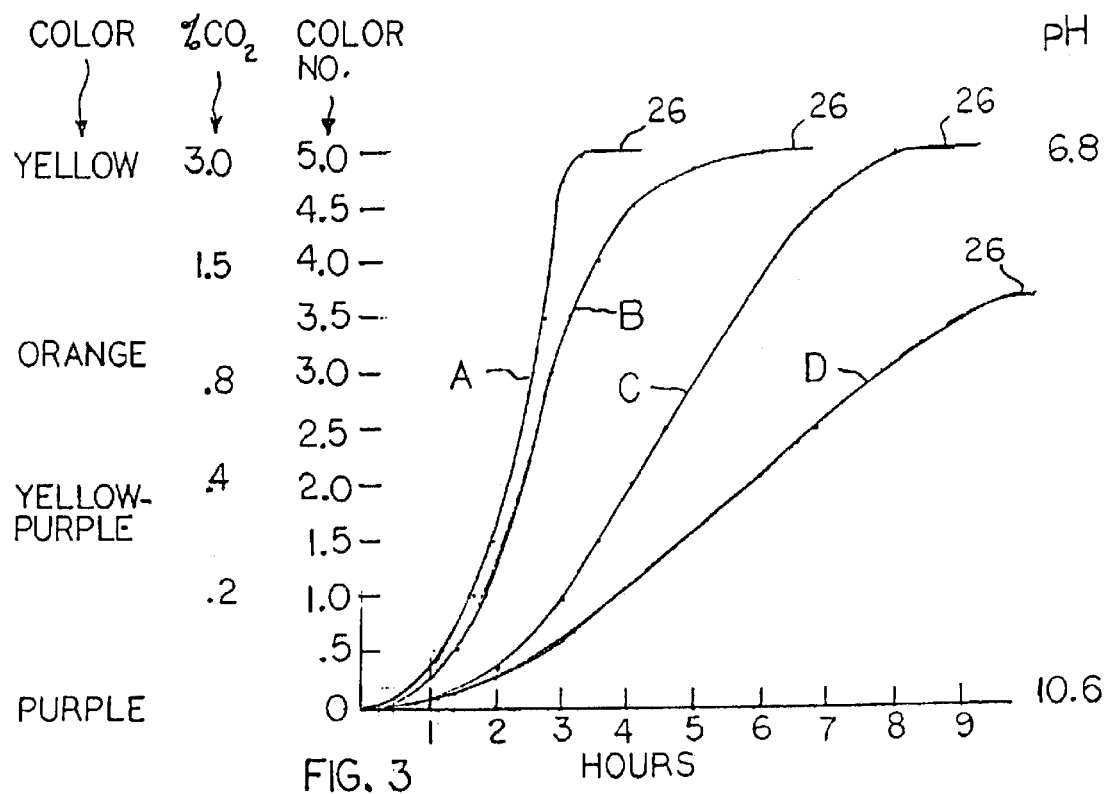

METHOD FOR DETERMINING THE STORABILITY OF A GRAIN OR OILSEED SAMPLE

FIELD OF THE INVENTION

This invention relates to a method for determining the storability or expected functional life of a grain or oilseed sample. The method can be practiced by grain storage operators, where the stored grain is exposed to fungus conditions that are not visible or readily discovered by cursory inspection of the grain.

BACKGROUND OF THE INVENTION

Grain and oilseeds (e.g. corn, wheat, oats, soybeans, alfalfa or rice) are often stored for prolonged periods of time, in excess of one year, before being shipped to the end user. During the storage period, the grain is subject to fungus attack that can lead to grain spoilage. In the early stage of the fungus attack, the spoilage is not readily detectable by human inspection of the grain. The grain can appear to be in an acceptable condition.

It would be desirable to have a method for discovering incipient grain spoilage before the spoilage becomes evident and thus possibly beyond the point where corrective measures (such as grain drying) can be taken. The present invention relates to a method of detecting the onset of grain spoilage before the spoilage condition is self evident.

SUMMARY OF THE INVENTION

The method of this invention utilizes the fact that fungal growth in grain is accompanied by the generation of gaseous carbon dioxide. By measuring the rate at which carbon dioxide is produced in a grain sample it is possible to form some useful conclusions as to the progress of the fungus attack and expected functional life of the grain. The term "functional life" is here used to mean the time that the grain can remain in storage before the grain experiences unacceptable deterioration.

The present invention uses a carbon dioxide detection system that is similar to a system disclosed in U.S. Pat. No. 5,320,807, issued to W. Brinton and M. Droffner on Jun. 14, 1994. The system of U.S. Pat. No. 5,320,807 is here modified to the extent that carbon dioxide measurements in the atmosphere proximate to the sample are taken periodically to establish a plot of carbon dioxide concentration versus time. The calculated rate of carbon dioxide generation can be used to form conclusions as to the expected functional life of the grain being sampled.

In preferred practice of the invention, the carbon dioxide measurements are supplemented by measurement of the moisture content of the grain being sampled The grain moisture content is an important influence on the rate of grain deterioration. A higher moisture content will generally accelerate fungus growth, so that higher moisture readings in conjunction with high carbon dioxide generation provide an important signal to the person charged with protecting the grain against fungus attack. For example, high CO2 production at low moisture content indicates a more deteriorated (i.e. more fungal growth) condition than that same CO2 production rate at high moister content.

Features and advantages of the invention will be apparent from the attached drawings and description of an illustrative method of practicing the invention.

BRIEF DESCRIPTION OF THE DRAWINGS

FIG. 1 is a sectional view taken through a grain sample container having a color change pH indicator that can be used in practice of the invention.

FIG. 2 is a sectional view taken at right angles to FIG. 1.

FIG. 3 is a graph showing rates of carbon dioxide generation for different grain samples placed in the grain sample container of FIG. 1.

DESCRIPTION OF A PREFERRED EMBODIMENT OF THE INVENTION

The sample container shown in FIGS. 1 and 2 may be generally similar to the container shown in U.S. Pat. No. 5,320,807, except that the container may have a different volumetric capacity and pH indicator material mass, commensurate with differences in the material being sampled. As shown in U.S. Pat. No. 5,320,807, the sampled material is moist compost. In the present invention, the sampled material is whole-kernel grain, e.g. corn, wheat, oats, soybeans, or alfalfa. The grain is sampled in a state representative of the grain storage environment from which the grain sample is taken. Typically, the moisture content of stored grain ranges between nine percent and twenty percent.

FIGS. 1 and 2 show a test sample container 10 having a transparent side wall 12 and removable closure (or lid) 14 that provides a closed sealed atmosphere within the container. Located within the container is a pH indicator device 16 that includes a non-reactive paddle 18 having a shallow recess 19 that contains a color change material (or patch) 20 responsive to pH changes in the container atmosphere 22 above a grain sample 24.

Color change material 20 includes a pH basic reactant component, (or buffer) e.g. sodium hydroxide plus sodium borate, and a combination of substances that change color in response to changes in the pH due to CO2 diffusing into the reactant component from the atmosphere 22. The color change substances can be the same as those used in the system described in U.S. Pat. No. 5,320,807, i.e. thymol blue and rosolic acid.

As described in U.S. Pat. No. 5,320,807, reactant patch 20 may be formed by pouring a heated reactant mixture into recess 19, using the recess as a mold cavity. The reactant mixture can be prepared by a series of steps that includes:
1. preparation of buffer with borax and sodium hydroxide
2. dissolving agar in the buffer by boiling
3. addition of dyes (pH indicators) and preservatives to the agar-buffer solution.
4. dispensing the hot agar-buffer solution onto the recess.
5. packaging the complete indicator device in a moisture-proof pouch to prevent drying or other change. In use of the test apparatus, a grain sample (e.g. shelled corn or wheat) is placed in the sample container, together with the pH indicator device 16. The indicator device is positioned so that color change material 20 is located in the gaseous atmosphere 22 above the grain sample. The container is then sealed.

Over time, fungal activity in the grain sample generates carbon dioxide and water, some of which are released from the grain sample into atmosphere 22. The gaseous $CO_2$ diffuses into the reactive device and reacts with the pH buffer in material 20 to lower the pH of material 20, generally in accordance with the carbon dioxide concentration in atmosphere 22.

Indicator material 20 exhibits color changes related to changes in its pH. As shown generally in FIG. 3, at a pH of about 10.3, the indicator material has a purple (or blue, if no rosolic acid dye is used) hue, whereas at a pH of about 6.8 the indicator material has a yellow coloration. As the pH is reduced from about 10.3 to about 6.8 the color progressively changes through red and orange (or green) hues, until the yellow coloration is reached. When the yellow coloration is reached the indicator material exhibits essentially no further color change.

Under the present invention the various colors associated with pH values in the 10.6 to 6.8 range are assigned different numbers, which vary according to the color perception capability of the human eye. As shown in FIG. 3, purple is assigned a color number of zero, whereas yellow is assigned a color number of five. The intervening colors are assigned color numbers between zero and five, according to the ability of the human eye to distinguish one color from another.

It might be noted that the use of numbers to distinguish one color from another is already known in the art. One known color numbering system is the Munsell system.

In practice of the present invention measurements of the color of indicator material 20 are periodically taken, e.g. every half hour from the time that the grain sample 24 is sealed in the container. At the time of each color measurement the associated color number is recorded on a graph of the type shown in FIG. 3. Alternatively, a single color reading is recorded at a specified time in accordance with a developed interpretation procedure, e.g. 4 or 24 hours.

Each color measurement can be performed by a human technician, using a color chart that has a color number associated with each color on the chart. The human technician visually compares the colors on the chart with the color of indicator material 20, and records the appropriate color number on the graph.

Color measurements can also be taken by mechanical mechanisms, e.g. a digital camera and computer. The color of indicator material 20 viewed by the digital camera can be digitized into a computer having a special program for translating the digitized color data into a color number (similar to the color number obtained by the human vision process). Alternatively, the color may be read by determining the reflectance of the reactant material spectrophotometrically using a variable wavelength spectrometer in which the preferred wavelength corresponds to the known color spectra of the dye used.

Whatever the procedure used to obtain the color numbers, such numbers can be plotted on a time-color number graph to obtain carbon dioxide release rate curves of the type depicted in FIG. 3. FIG. 3 illustratively shows four curves A, B, C and D that represent expected carbon dioxide release rates from four different grain samples having the same mass.

Referring to curve A, the complete color change, from purple (or blue) to yellow, is achieved at approximately three hours (measured from the time that the grain sample is sealed in container 10). Horizontal line 26 on curve A denotes the end of the color change, determined by the nature of the color change substances in indicator material 20. The expected functional life of the grain sample is directly proportional to the total time interval that it takes the indicator material 20 to change from purple (or blue) to yellow.

Curve A is representative of a grain sample having an undesirably high carbon dioxide release rate.

Curve B plots the color change produced by a second grain sample having a lower carbon dioxide release rate. In this case, about five and one half hours is required for the indicator to achieve a complete color change (from purple to yellow).

Curves C and D plot color changes produced by other grain samples having still lower carbon dioxide release rates. The curves can provide the technician with information on the carbon dioxide release rate and the probable deterioration of the grain being sampled, even when the fungal damage is not yet visible to the naked eye.

As regards curves A, B, C and D, curve A represents a grain sample with an unacceptably high carbon dioxide release rate, whereas curves C and D represent grain samples having acceptable carbon dioxide release rates. Curve B represents a carbon dioxide release rate that is marginally acceptable. Calibration work with grain samples having known fungal decay conditions at specific moisture contents is required to provide reference curves for field operations.

The demarcation between an acceptable carbon dioxide release rate and unacceptable release rate is somewhat subjective. With the proposed color indicator system, it is possible in many cases to predict the expected shelf life in terms of days. However, with some experience in using the method of this invention combined with a knowledge of the moisture content of the grain sample, an experienced technician can obtain useful information for predicting grain storage damage, as well as the amount of time that the grain can remain in storage without dangerous spoilage. In some cases the information from the proposed sampling procedure can be used to make a determination on the need for drying the stored grain (to prevent spoilage).

The sampling method of this invention is most useful when carried out in conjunction with measurements of the grain moisture content (with a moisture meter or by drying and weighing a grain sample). The expected functional life of a grain sample is inversely proportional to the grain moisture content. In general, a high grain moisture content in conjunction with a high carbon dioxide release rate (per curve A) represents a more serious threat to grain integrity than a high carbon dioxide release rate alone (without a high grain moisture content). Similarly, a high carbon dioxide release rate with moderately low moisture content may be indicative of previous grain damage. Grain damage may result from physical abuse such as from handling methods, or from prior wetting and drying, and the like.

Moisture in stored grain can be a result of several factors, such as incomplete drying of the grain prior to storage, a humid atmosphere in the grain storage chamber, and/or fungal attack. During fungal attack the breakdown of organic matter (e.g. starch) in the grain produces carbon dioxide and water.

The present invention concerns primarily the method of determining carbon dioxide release rates in grain samples, using a color change indicator material responsive to pH changes resulting from release of carbon dioxide from the grain sample. The ancillary measurement of grain moisture content adds to the value and usefulness of predicting the storability of the grain based on the carbon dioxide release rate.

It will be appreciated that the method of carbon dioxide measurement can be varied somewhat, while still practicing the invention. Preferably, the color measurements are performed on a timed basis, e.g. one half hour intervals or one hour intervals. The total test period can range, preferably, from about four hours (per curve A) up to about 24 hours (per curves C and D). The limit on the test period occurs when indicator material 20 no longer exhibits a perceptible color change, because the yellow color limit has been reached.

The mass of the grain sample is preferably selected so that the carbon dioxide concentration in atmosphere 22 varies from about zero percent to about three percent. The ionic strength of the buffer in the reactant device is selected to ensure color change over a convenient time period.

What is claimed is:

1. A method for determining the expected functional life of a grain sample taken from stored grain, wherein the expected life is predicted from the rate of release of carbon dioxide from the grain sample at a known moisture content, said method comprising:

measuring the moisture content of the grain sample;

placing the aforementioned grain sample in a container so that a gaseous atmosphere exists in the container above the sample;

providing a color change indicator responsive to pH changes, and positioning the indicator in the gaseous atmosphere in the container;

sealing the grain sample and color change indicator in the container;

assigning a color number to each color on the indicator;

periodically viewing the indicator and at the same time recording the color of the indicator as the appropriate color number until the indicator has achieved a predetermined color change wherein the indicator changes color due to the release of carbon dioxide from the grain sample into the gaseous atmosphere;

plotting the color numbers versus the corresponding times when the indicator is being viewed;

noting the total time interval required for the indicator to achieve the predetermined color change; and predicting the expected functional life of the grain sample, based on the total time interval for the indicator to achieve the predetermined color change, and the measured moisture content; wherein the expected functional life is directly proportional to the total time interval, and inversely proportional to the grain moisture content.

2. The method of claim 1, wherein the step of viewing the indicator and recording the appropriate color number is repeated until the indicator no longer exhibits a color change.

3. The method of claim 1, wherein the step of viewing the indicator and recording the appropriate color number is repeated until the indicator achieves a color coincident with the limit of the indicator pH response.

4. The method of claim 1, wherein the step of viewing the indicator involves the use of a variable wavelength spectrometer.

* * * * *